US010793854B2

(12) United States Patent
Murase et al.

(10) Patent No.: US 10,793,854 B2
(45) Date of Patent: *Oct. 6, 2020

(54) SKIN AND HAIR COLOR-CONTROLLING FACTOR

(71) Applicant: Kao Corporation, Chuo-ku, Tokyo (JP)

(72) Inventors: Daiki Murase, Mason, OH (US); Akira Hachiya, Utsunomiya (JP)

(73) Assignee: Kao Corporation, Tokyo (JP)

( * ) Notice: Subject to any disclaimer, the term of this patent is extended or adjusted under 35 U.S.C. 154(b) by 450 days.

This patent is subject to a terminal disclaimer.

(21) Appl. No.: 15/357,459

(22) Filed: Nov. 21, 2016

(65) Prior Publication Data
US 2017/0067054 A1 Mar. 9, 2017

Related U.S. Application Data

(62) Division of application No. 13/882,669, filed as application No. PCT/JP2011/075064 on Oct. 31, 2011, now Pat. No. 9,561,167.

(30) Foreign Application Priority Data

Nov. 1, 2010 (JP) .................. 2010-245039

(51) Int. Cl.
C12N 15/113 (2010.01)
G01N 33/50 (2006.01)
C12Q 1/6876 (2018.01)
C07K 14/47 (2006.01)
A61K 8/60 (2006.01)
A61Q 5/06 (2006.01)
A61Q 19/00 (2006.01)
A61K 48/00 (2006.01)

(52) U.S. Cl.
CPC ............ *C12N 15/113* (2013.01); *A61K 8/606* (2013.01); *A61Q 5/065* (2013.01); *A61Q 19/00* (2013.01); *C07K 14/4702* (2013.01); *C12Q 1/6876* (2013.01); *G01N 33/5023* (2013.01); *G01N 33/5044* (2013.01); *A61K 48/005* (2013.01); *C12N 2310/14* (2013.01); *C12Q 2600/136* (2013.01); *C12Q 2600/148* (2013.01); *C12Q 2600/158* (2013.01)

(58) Field of Classification Search
CPC .................................................... C12N 15/113
See application file for complete search history.

(56) References Cited

U.S. PATENT DOCUMENTS 8,927,517 B2 1/2015 Murase et al.
2012/0034613 A1* 2/2012 Gopaul .................. A61K 45/06
435/6.12
2013/0324587 A1 12/2013 Murase et al.

FOREIGN PATENT DOCUMENTS

EP        2 250 993 A1    11/2010
JP      2011-208964 A     10/2011
JP         5037515 B       5/2016
WO    WO 2010/029343 A2   3/2010

OTHER PUBLICATIONS

International Search Report (ISR) for PCT/JP2011/075064; I.A. fd: Oct. 31, 2011, dated Jan. 31, 2012 from the Japanese Patent Office, Tokyo, Japan.
International Preliminary Report on Patentability (IPRP), Chapter I of the Patent Cooperation Treaty, including the Written Opinion for PCT/JP2011/075064; I.A. fd: Oct. 31, 2012, dated May 13, 2013, from the International Bureau of WIPO, Geneva, Switzerland.
Miyachi, Y. et al., "Chapter IV: Pharmacology and the clinic of the whitening agent—The whitening agent general remarks—external preparation for whitening," in Advanced Cosmetic Dermatology No. 1 Whitening Strategy, Pharmacology and Medical Practice of Whitening Agents, pp. 95-116 (2006), Nankodo Co., Ltd., Tokyo, Japan, pp. 99-101.
Thong, HY et al., "The patterns of melanosome distribution in keratinocytes of human skin as one determining factor of skin colour," Br J Dermatol 149(3): 498-505, (Sep. 2003), Blackwell Scientific Publications, Oxford, England.
Lin, CB, et al., "LIGR, a protease-activated receptor-2-derived peptide, enhances skin pigmentation without inducing inflammatory processes," Pigment Cell Melanoma Res 21(2): 172-183, (Apr. 2008), Blackwell Munksgaard, Oxford, England.
Byers, HR et al., "Role of cytoplasmic dynein in perinuclear aggregation of phagocytosed melanosomes and supranuclear melanin cap formation in human keratinocytes," J Invest Dermatol 121(4): 813-820 (Oct. 2003), Nature Publishing Group, New York.
Byers, HR et al., "Requirement of dynactin p150(Glued) subunit for the functional integrity of the keratinocyte microparasol," J Invest Dermatol 127(7): 1736-1744 (Jul. 2007), Nature Publishing Group, New York.
Singh, SK et al., "Melanin transfer in human skin cells is mediated by filopodia—a model for homotypic and heterotypic lysosome-related organelle transfer," FASEB J 24: 3756-3769 (Oct. 2010), The Federation, Bethesda, MD.
Ebanks, JP et al., "Epidermal keratinocytes from light vs. dark skin exhibit differential degradation of melanosomes," J Invest Dermatol 131(6): 1226-1233, (Jun. 2011), Nature Publishing Group, New York.
Vaughan, KT et al., "Colocalization of cytoplasmic dynein with dynactin and CLIP-170 at microtubule distal ends," J. Cell Sci 112: 1437-1447 (May 1999), Company of Biologists, Cambridge, England.
Yang, M et al., "Rab7b, a novel lysosome-associated small GTPase, is involved in monocytic differentiation of human acute promyelocytic leukemia cells," Biochem Biophys Res Commun 318(3): 792-799 (Jun. 2004), Academic Press, San Diego, CA.

(Continued)

*Primary Examiner* — Antonio Galisteo Gonzalez
(74) *Attorney, Agent, or Firm* — Sterne, Kessler, Goldstein & Fox, P.L.L.C.

(57) ABSTRACT

Provided are a gene involved in the regulation of the amount of melanin in keratinocytes, and the control of the color of skin or hair, the gene being selected from the group consisting of ATG7 gene, RAB11A gene, CLIP-170 gene, Rubicon gene and RAB7B gene, and a molecule encoded by the gene.

2 Claims, 5 Drawing Sheets

(56) References Cited

OTHER PUBLICATIONS

Wang, Y et al., "Lysosome-associated small Rab GTPase Rab7b negatively regulates TLR4 signaling in macrophages by promoting lysosomal degradation of TLR4," Blood 110: 962-971 (Aug. 2007), Am. Soc. Hematology, Washington, DC.
Yao, M et al, "Late Endosome/Lysosome-Localized Rab7b Suppresses TLR9-Initiated Proinflammatory Cytokine and Type I IFN Production in Macrophages," J Immunol 183: 1751-1758, (Aug. 2009), American Association of Immunologists, Baltimore, MD.
Progida, C et al., "Rab7b controls trafficking from endosomes to the TGN,"J Cell Sci 123: 1480-1491, (May 2010), Company of Biologists, Cambridge, England.
Matsunaga, K et al., "Two Beclin 1-binding proteins, Atg14L and Rubicon, reciprocally regulate autophagy at different stages," Nat Cell Biol; 11(4): 385-396, (Apr. 2009), Macmillan Magazines Ltd., London, England.
Bryant, DM et al., "A molecular network for de novo generation of the apical surface and lumen," Nat Cell Biol 12(11): 1035-1045, (Nov. 2010), Macmillan Magazines Ltd., London, England.
Ishida-Yamamoto, A et al., "Rab11 is associated with epidermal lamellar granules," J Invest Dermatol 127(9): 2166-2170 (Sep. 2007), Nature Publishing Group, New York.
Komatsu, M et al., "Impairment of starvation-induced and constitutive autophagy in Atg7-deficient mice," J. Cell Biol. 169: 425-434 (May 2005), Rockefeller University Press, New York.
Raymond, A-A et al., "Lamellar Bodies of Human Epidermis: Proteomics Characterization by High Throughput Mass Spectrometry and Possible Involvement of CLIP-170 in their Trafficking/Secretion," Mol. Cell. Proteomics 7: 2151-2175 (Nov. 2008), American Society for Biochemistry and Molecular Biology, Bethesda, MD.
Gebhardt, C et al., "c-Fos-dependent induction of the small ras-related GTPase Rab11a in skin carcinogenesis," Am J Pathol 167(1): 243-253 (Jul. 2005), American Assn. of Pathologists, Philadelphia, PA.
Babiarz-Magee, L et al., "The expression and activation of protease-activated receptor-2 correlate with skin color," Pigment Cell Res 17(3): 241-251 (Jun. 2004), Munksgaard International Publishers, Copenhagen, Denmark.
Kirkin, V et al., "A role for NBR1 in autophagosomal degradation of ubiquitinated substrates," Mol Cell 33(4): 505-516, (Feb. 2009), Cell Press, Cambridge, MA.
Levine B et al., "Autophagy in the pathogenesis of disease," Cell 132(1): 27-42, (Jan. 2008), Cell Press, Cambridge, MA.
Mizushima, N et al., "Autophagy fights disease through cellular self-digestion," Nature 451(7182): 1069-1075, (Feb. 2008), Nature Publishing Group, New York, NY.
Mizushima, N et al., "Methods in mammalian autophagy research," Cell 140(3): 313-326, (Feb. 2010), Cell Press, Cambridge, MA.
Mizushima, N et al., "How to interpret LC3 immunoblotting," Autophagy 3(6): 542-545, (Nov. 2007), Landes Bioscience, Georgetown, TX.
Paine, C et al., "An alternative approach to depigmentation by soybean extracts via inhibition of the PAR-2 pathway," J Invest Dermatol 116(4): 587-595, (Apr. 2001), Williams & Wilkins, Baltimore, MD.
Rubinsztein, DC, "The roles of intracellular protein-degradation pathways in neurodegeneration," Nature 443(7113): 780-786, (Oct. 2006), Nature Publishing Group, New York, NY.
Seiberg, M et al., "Inhibition of melanosome transfer results in skin lightening." J Invest Dermatol 115(2): 162-167, (Aug. 2000), Williams & Wilkins, Baltimore, MD.
Seiberg, M et al., "The protease-activated receptor 2 regulates pigmentation via keratinocyte-melanocyte interactions," Exp Cell Res 254(1): 25-32, (Jan. 2000), Academic Press, New York, NY.
Seiberg, M, "Keratinocyte-melanocyte interactions during melanosome transfer," Pigment Cell Res 14(4): 236-242, (Aug. 2001), Blackwell Munksgaard, Oxford, England.

International Search Report (ISR) for PCT/JP2013/062439; I.A. fd: Apr. 26, 2013, dated Aug. 2013 from the Japanese Patent Office, Tokyo, Japan.
Sceti K.K., "Detoxification of cells by the automatic fuzzy," ("Seti Kabushiki Kaisha, Auto Fuzzy ni yoru Saibo no detox 'CELLDETOX'"), Fragrance J, 2010, vol. 38, No. 8, pp. 121-122, Fureguransujanaru Co., Inc., Japan.
Schiaffino, MV, "Signaling pathways in melanosome biogenesis and pathology,"Int J Biochem Cell Biol, Jul. 2010; 42(7): 1094-1104, Elsevier, Amsterdam, Netherlands.
Matsunaga, K et al., "Evolution and relationship to diseases of autophagic driving/regulation machinery," (Shikkan hi Taiko suru Auto Fuzzy Auto Fuzzy no Kudo•Seigyo Kiko no Shinka to Shikkan tono Kakawari), Experimental Medicine, 2009, vol. 27, No. 18, pp. 2930-2936, Yodosha Company Limited, Tokyo, Japan.
Itakura, E. et al., ""Physiological role and regulation of mammalian autophagy," (Shikkan ni Taiko suru Auto Fuzzy Honyurui Auto Fuzzy no Seigyo to Seiri Kino") Experimental Medicine, 2009, vol. 27, No. 18, pp. 2937-2942, Yodosha Company Limited, Tokyo, Japan.
Zhuang, Shuzhen et al., "Study on the IZP3 mRNA expression after siRNA interference," Chinese Agricultural Science Bulletin 23(6):23-27 (Jun. 30, 2007), Zhongguo nong xue hui, Beijing, China.
Jiang, Jian et al., "Inhibitory effect of interfering RNA targeting HIF-1α and VEGF on retinal neovascularization in the mouse," Chin. J. Opthalmol. 44(10):921-928 (Oct. 31, 2008), Chinese Medical Association, Beijing, China.
Ou, Shu-An et al., "Inhibitory effect of Slug gene silencing with siRNA on pancreatic cancer," World Chinese Journal of Digestology, Issue 17, pp. 1713-1719 (Jun. 18, 2009), WJC Press, Beijing, China.
Ho, H. et al., "WIPI1 Coordinates Melanogenic Gene Transcription and Melanosome Formation via TORC1 Inhibition," J. Biol. Chem., Apr. 2011; 286: 12509-12523, Am. Soc. for Biochem. and Molec. Biol., Rockville, MD.
Van den Boorn, JG et al., "Skin-depigmenting agent monobenzone induces potent T-cell autoimmunity toward pigmented cells by tyrosinase haptenation and melanosome autophagy," J Invest Dermatol, Jun. 2011; 131(6): 1240-1251, Nature Publishing Group, NY.
U.S. Appl. No. 13/858,374, Excerpted file history: Applicants'Amendment and Reply (filed Apr. 21, 2014) and the non-final Office action (dated Dec. 31, 2013), United States Patent and Trademark Office, Alexandria, VA.
Extended European Search report for EP Appl. No. 11837973.4, including the supplementary European search report and the European search opinion, dated Apr. 4, 2014, European Patent Office, Munich, Germany.
Lacour, JP, "Culturing Human Melanocytes," Pathol Biol (Paris), Feb. 1992; 40(2): 114-120, Elsevier, Paris, France.
Duval, C et al., "Keratinocytes control the pheo/eumelanin ratio in cultured normal human melanocytes," Pigment Cell Res, Dec. 2002; 15(6): 440-446, Munksgaard International Publishers, Copenhagen, Denmark.
Ganesan, AK et al., "Genome-wide siRNA-based functional genomics of pigmentation identifies novel genes and pathways that impact melanogenesis in human cells," PLoS Genet, Dec. 2008; 4(12): e1000298, 12 pages, www.plosgenetics.org, Public Library of Science, San Francisco, CA.
Baxter, LL et al., "Networks and pathways in pigmentation, health, and disease," Wiley Interdiscip Rev Syst Biol Med, Nov. 2009; 1(3): 359-371, John Wiley & Sons, Hoboken, NJ.
Delevoye, C et al., "AP-1 and KIF13A coordinate endosomal sorting and positioning during melanosome biogenesis," J. Cell Biol., Oct. 2009; 187: 247-264, Rockefeller University Press, New York, NY.
Deneka, M, et al., "Regulation of membrane transport by rab GTPases," Crit Rev Biochem Mol Biol, Jan. 2003; 38(2): 121-142, Informa Healthcare, London, England.
Murase, D et al., "Autophagy has a significant role in determining skin color by regulating melanosome degradation in keratinocytes," J Investigative Dermatology 133(10):2416-2424; Oct. 2013; published online May 9, 2013; Nature Publishing Group, New York, NY.

(56) References Cited

OTHER PUBLICATIONS

U.S. Appl. No. 13/858,374, Excerpted file history: Notice of Allowance dated Nov. 6, 2014, United States Patent and Trademark Office, Alexandria, VA.
Extended European search report including the supplementary European search report and the European search opinion for EP Appl. No. 13782429.8, dated Dec. 3, 2015, European Patent Office, Munich, Germany.
Aymard, E et al., "Autophagy in human keratinocytes: an early step of the differentiation?" Exp Dermatol 20(3):263-268 (Mar. 2011), John Wiley & Sons.
Emoto, M et al., "A role for kinesin in insulin-stimulated GLUT4 glucose transporter translocation in 3T3-L1 adipocytes," J Biol Chem. Apr. 6, 2001;276(14):10677-82. Epub Jan. 5, 2001, American Society for Biochemistry and Molecular Biology, Baltimore, MD.
Griner, R et al., "Increased Rab11a expression in differentiating primary mouse keratinocytes," Abstracts for the 60th Annual Meeting of the Society for Investigative Dermatology, Chicago, Ill, May 5-9, 1999, J Invest Dermatol. 112:576 (abstract #320) (1999), Elsevier, New York.
Boyce, ST et al., "Calcium-regulated differentiation of normal human epidermal keratinocytes in chemically defined clonal culture and serum-free serial culture," J Invest Dermatol. Jul. 1983;81(1 Suppl):33s-40s, Elsevier, New York.

* cited by examiner

SKIN AND HAIR COLOR-CONTROLLING FACTOR

FIELD OF THE INVENTION

The present invention relates to the regulation of the amount of melanin in keratinocytes, and the control of the color of skin or hair.

BACKGROUND OF THE INVENTION

Various factors for determining the color of skin or hair have been reported, but among them, the amount or quality of melanin that is present in the epidermis is considered to contribute to the color of skin or hair to a large extent. That is, color formation in skin or hair is believed to be largely affected when melanin, which is produced in a cell organelle called melanosome in the pigment cells (melanocytes), is transferred to keratinocytes in the epidermis or hair follicles, and spreads over the entirety of the epidermis or hair. The amount of melanin produced by those melanocytes has been known for long as a factor associated with the color of skin or hair of an individual.

Conventional skin whitening agents have been developed primarily for targeting melanin production in melanocytes. For example, Non-Patent Document 1 reports skin whitening agents having an action of inhibiting the enzymatic activity of tyrosinase, which is an enzyme involved in the conversion of tyrosine, a melanin precursor, to melanin and thereby suppressing melanin production, such as ascorbic acid, arbutin, and kojic acid.

On the other hand, it has also been reported that depending on the differences in skin color, differences in the form of existence or the state of maturity of melanin in keratinocytes are also recognized (Non-Patent Document 2). That is, a possibility that the melanin dynamics in keratinocytes may be in charge of a certain role in the determination of skin color. In the reports published so far, it has been suggested that a receptor molecule, PAR-2, is involved in the uptake (phagocytosis) of melanin in keratinocytes, and there is a possibility of the control of skin color by regulating the activity of the receptor molecule (Non-Patent Document 3). Furthermore, it has been suggested that protein molecules Dynein and Dynactin participate in the localization of melanin in keratinocytes after melanin is transferred to the keratinocytes (Non-Patent Documents 4 and 5). More recently, it has been suggested that a protein molecule, MyoX, which is involved in the formation of a cellular structure called filopodium, is involved in both the transfer of melanin from a melanocyte to a keratinocyte and the transfer of melanin from a keratinocyte to a keratinocyte (Non-Patent Document 6). However, the mechanism of uptake, transport and metabolism by keratinocytes of the melanin (melanosome) produced in melanocytes has not yet been sufficiently elucidated, and the role involving in skin color has not been verified.

Furthermore, recently, it has been suggested, from an investigation using keratinocytes derived from different races, that there are racial differences in the metabolic capacity of melanin that has been incorporated in the keratinocytes (Non-Patent Document 7). This article reports that melanin is prone to be decomposed in Caucasian-derived epidermal cells, based on the results obtained by incorporating a melanin that was labeled with a fluorescent substance into epidermal cells, and then observing the progress of extinction of fluorescence in the epidermal cells. However, nothing is mentioned regarding the mechanism contributing to the decomposition or any particular factor.

CLIP-170, RAB7B, Rubicon, RAB11A, and ATG7 are known as molecules that participate in the transport or localization of vesicles, or in the decomposition or self-digestion of vesicles (Non-Patent Documents 8 to 16). However, it has not been made clear as to whether these molecules are involved in the melanin dynamics in keratinocytes, for example, uptake, transport, localization or accumulation, excretion or decomposition of melanin.

CITATION LIST

Non-Patent Document

Non-Patent Document 1: Bihaku Senryaku I V. Bibakuzai no Yakuri to Rinsho (Whitening Strategy IV. Pharmacology and Medical Practice of Whitening Agents; Nankodo Co., Ltd.), p. 95-116

Non-Patent Document 2: Thong et al., (2003) Br. J. Dermatol. 149:498-505

Non-Patent Document 3: Lin et al., (2008) Pigment Cell Melanoma Res. 21:172-183

Non-Patent Document 4: Byers et al., (2003) J. Invest. Dermatol. 121:813-820

Non-Patent Document 5: Byers et al., (2007) J. Invest. Dermatol. 127:1736-1744

Non-Patent Document 6: Singh et al., (2010) FASEB J. 24:3756-3769

Non-Patent Document 7: Ebanks et al., (2011) J. Invest. Dermatol. 131:1226-1233

Non-Patent Document 8: Vaughan et al., (1999) J. Cell Sci. 112:1437-1447

Non-Patent Document 9: Yang et al., (2004) Biochem. Biophys. Res. Commun. 318:792-799

Non-Patent Document 10: Wang et al., (2007) Blood 110:962-971

Non-Patent Document 11: Yao et al., (2009) J. Immunol. 183:1751-1758

Non-Patent Document 12: Progida et al., (2010) J. Cell Sci. 123:1480-1491

Non-Patent Document 13: Matsunaga et al., (2009) Nat. Cell Biol. 11:385-396

Non-Patent Document 14: Bryant et al., (2010) Nat. Cell Biol. 12:1035-1045

Non-Patent Document 15: Ishida-Yamamoto et al., (2007) J. Invest. Dermatol. 127:2166-2170

Non-Patent Document 16: Komatsu et al., (2005) J. Cell Biol. 169:425-434

SUMMARY OF THE INVENTION

According to an embodiment, the present invention provides, hereinbelow, a method for evaluating and/or selecting an agent for regulating the amount of melanin in keratinocytes, the method comprising:

administering a test substance into cells;

measuring any change in the expression of at least one gene selected from the group consisting of ATG7, RAB11A, CLIP-170, Rubicon and RAB7B, or any change in the expression or activity of at least one of the molecules encoded by the genes, in the cells;

evaluating the action of regulating the amount of melanin of the test substance, on the basis of the results of the measurement; and selecting the test substance as an agent for regulating the amount of melanin in keratinocytes, on the basis of the results of the evaluation.

According to another embodiment, the present invention provides, hereinbelow, a method for evaluating and/or selecting an agent for the control of the color of skin or hair, the method comprising:
administering a test substance into cells;
measuring any change in the expression of at least one gene selected from the group consisting of ATG7, RAB11A, CLIP-170, Rubicon and RAB7B, or any change in the expression or activity of at least one of the molecules encoded by the genes, in the cells;
evaluating the action of controlling the color of skin or hair of the test substance, on the basis of the results of the measurement; and
selecting the test substance as an agent for the control of the color of skin or hair, on the basis of the results of the evaluation.

According to still another embodiment, the present invention provides a method for regulating the amount of melanin in keratinocytes, the method comprising regulating the expression of at least one gene selected from the group consisting of ATG7, RAB11A, CLIP-170, Rubicon and RAB7B, or the expression or activity of at least one of the molecules encoded by the genes, in keratinocytes where regulation of the amount of melanin is desired.

According to still another embodiment, the present invention provides a method for controlling the color of skin or hair in a test subject, the method comprising regulating the expression of at least one gene selected from the group consisting of ATG7, RAB11A, CLIP-170, Rubicon and RAB7B, or the expression or activity of at least one of the molecules encoded by the genes, in the keratinocytes of a test subject who desires to control the color of skin or hair.

According to another embodiment, the present invention provides use of a gene selected from the group consisting of ATG7, RAB11A, CLIP-170, Rubicon and RAB7B, or a molecule encoded by the relevant gene, for regulating the amount of melanin in keratinocytes.

According to still another embodiment, the present invention provides use of a gene selected from the group consisting of ATG7, RAB11A, CLIP-170, Rubicon and RAB7B, or a molecule encoded by the relevant gene, for controlling the color of skin or hair.

According to another embodiment, the present invention provides a gene that controls the color of skin or hair, the gene being selected from the group consisting of ATG7 gene, RAB11A gene, CLIP-170 gene, Rubicon gene, and RAB7B gene, and being involved in the regulation of the amount of melanin in keratinocytes.

DETAILED DESCRIPTION OF THE INVENTION

Figure 1:
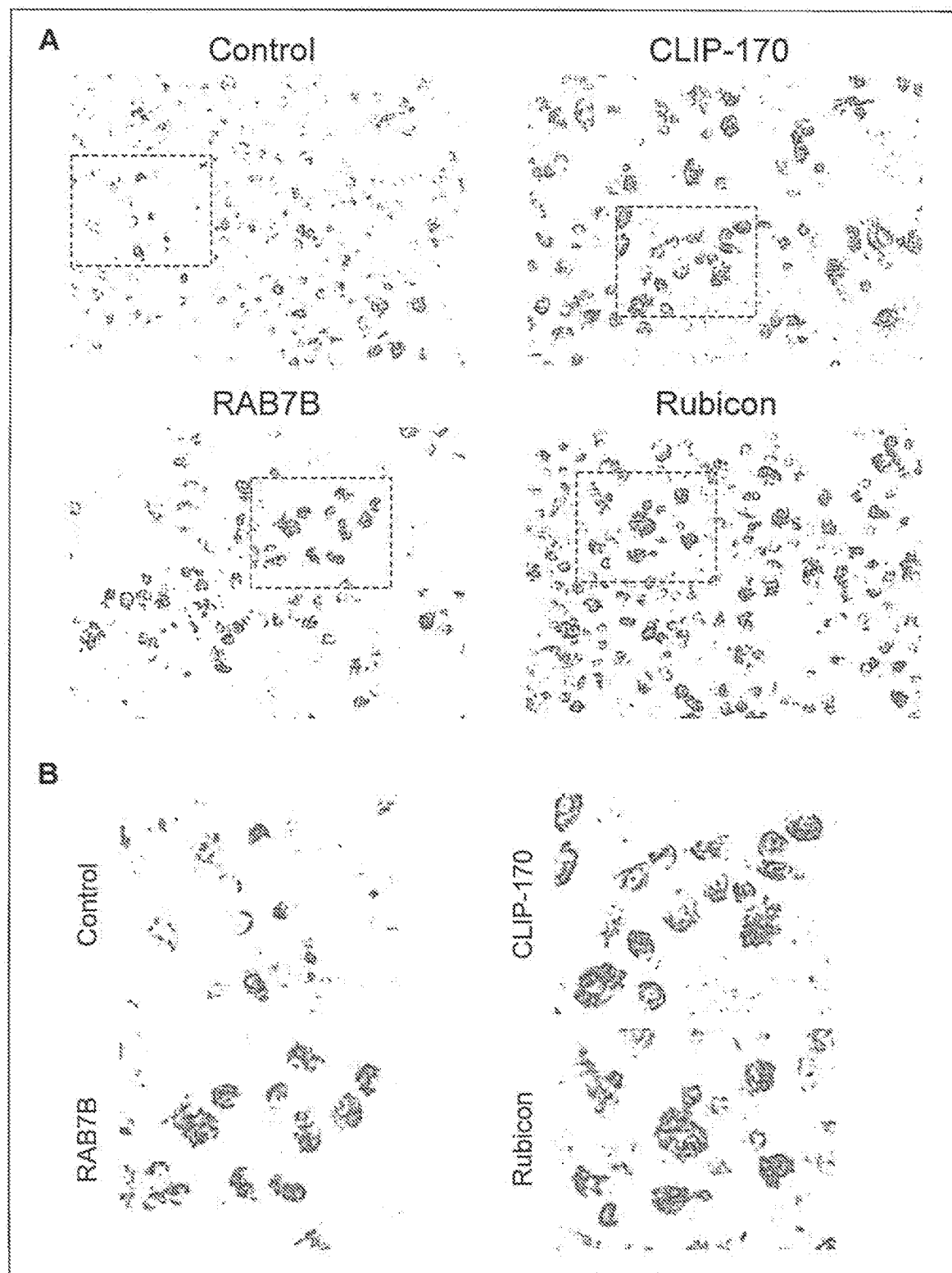
FIG. 1 is microscopic images illustrating the melanin distribution in keratinocytes after suppression of the expression of CLIP-170, RAB7B or Rubicon gene, in which A. Upper left image: control, upper right image: suppression of CLIP-170, lower left: suppression of RAB7B, lower right: suppression of Rubicon, and B. Magnified images of the areas surrounded by rectangles in the images of A.

The present invention relates to a factor which participates in the localization, accumulation, excretion or decomposition of melanin in keratinocytes, and is involved in the regulation of the amount of melanin in keratinocytes and the control of the color of skin or hair. Furthermore, the present invention relates to a method for regulating the amount of melanin in keratinocytes by using the relevant factor; a method for controlling the color of skin or hair; and a method for evaluating and/or selecting an agent for regulating the amount of melanin, or an agent for the control of the color of skin or hair, in keratinocytes by using the relevant factor.

In order to clarify the relations between the color of skin or hair and the gene expression in keratinocytes, the inventors of the present invention searched for a gene which is involved in the regulation of the amount of melanin in keratinocytes, and conducted an investigation on the effect of the expression of the relevant gene on the melanin dynamics in keratinocytes. Then, the inventors found several genes involved in the localization, accumulation, excretion or decomposition of melanin in keratinocytes, and confirmed that there is a high correlation between the expression level of those genes and the skin color. From these results, the inventors of the present invention found that the amount of melanin in keratinocytes or the color of skin or hair can be controlled using the relevant genes or expression products thereof.

According to the present invention, there is provided a gene that controls the color of skin or hair, which is capable of controlling the color of skin or hair by affecting the localization, accumulation, excretion and decomposition of melanin in keratinocytes. By regulating the expression or activity of the relevant gene or an expression product thereof, the amount and distribution of melanin in keratinocytes can be regulated, and the color of skin or hair can be controlled. Furthermore, the relevant gene or an expression product thereof is useful for the development of an agent for the control of the color of skin or hair, for example, a whitening agent, a tanning agent, a hair coloring or bleaching agent, or a dye for gray hair, since a material capable of controlling the color of skin or hair can be evaluated and/or selected by employing the expression or activity of the relevant gene or an expression product thereof as an indicator.

The present invention provides a gene that controls the color of skin or hair, which is selected from the group consisting of ATG7 gene, RAB11A gene, CLIP-170 gene, Rubicon gene, and RAB7B gene.

The genes listed above are registered in a known database as indicated in the following Table 1, but participation thereof in the melanin dynamics in keratinocytes, for example, uptake, transport, localization, accumulation, excretion or decomposition of melanin, has not been known hitherto.

TABLE 1

| Gene symbol | Gene name | | Gene ID (NCBI) | Accession No. |
|---|---|---|---|---|
| CLIP-170 | CLIP1 | Cytoplasmic Linker Protein-170 CAP-GLY domain containing linker protein 1 | 6249 | NM_002956.2 |
| RAB7B | RAB7B | Ras-related protein Rab-7b | 338382 | NM_001164522 |
| Rubicon | KIAA0226 (RUBICON) | KIAA0226 (RUBICON) | 9711 | NM_001145642.1 |
| RAB11A | RAB11A | Ras-related protein Rab-11a | 8766 | NM_004663.3 |
| ATG7 | ATG7 | ATG7 autophagy related 7 homolog (S. cerevisiae) | 10533 | NM_006395.2 |

CLIP-170 has been traditionally known as a molecule which directly controls intracellular transport of vesicles by tethering vesicles to microtubules. More specifically, CLIP-170 is known to mediate the interaction between a motor protein called Dynein or Dynactin and the microtubules (Vaughan et al., 1999, J. Cell Sci. 112, 1437-1447).

RAB7B is a molecule which was first identified in 2004, and belongs to the Rab GTPase family, a low molecular weight G protein family, that is deeply involved in the transport of vesicles (Yang et al., 2004, Biochem. Biophys. Res. Commun. 318, 792-799). It is reported that RAB7B is abundantly expressed primarily in immune cells such as monocytes, macrophages and dendritic cells, and participates in the endocytosis of TLR4 (Toll-like receptor 4) or TLR9 (Toll-like receptor 9), which are both involved in immune control (Wang et al., 2007, Blood 110, 962-971; and Yao et al., 2009, J. Immunol. 183, 1751-1758). Furthermore, it is also known that in Hela cells, RAB7B regulates the maturation of Cathepain-D, which is a vesicle degrading enzyme, and normal transport to lysosome, which is an intracellular digestive organ, can be interrupted by suppressing the expression of RAB7B (Progida et al., 2010, J. Cell Sci. 123, 1480-1491).

Rubicon has been recently reported as a molecule which suppresses self-digestion (autophagy) in cells (Matsunaga et al., 2009, Nat. Cell Biol. 11, 385-396).

It is known that RAB11A belongs to the Rab GTPase family, a small G-protein family, that is deeply involved in the transport of vesicles similar to RAB7B, and is involved in the recycling of vesicles, formation of cell polarity, and the transport of various vesicles, such as exocytosis (Bryant et al., 2010, Nat. Cell Biol. 12, 1035-1045). Furthermore, it has also been reported that RAB11A is involved in extracellular secretion of lamellar granules (lamellar bodies) in the epidermal granular layer (Ishida-Yamamoto et al., 2007, J. Invest Dermatol. 127, 2166-2170).

ATG7 is one of factors that control autophagy. Autophagy, which is also called self-digestion, is a mechanism by which large protein structures such as intracellular organelles are enveloped with membranes and the resultant is fused with lysosome, which is a protein degrading organelle, thereby decomposing the content. ATG7 is one of autophagy-related factors, and is known to be involved in the formation of autophagosome (Komatsu et al., 2005, J. Cell Biol. 169, 425-434).

As will be exemplified in the following Examples, when the expressions of ATG7 gene, RAB11A gene, CLIP-170 gene, Rubicon gene and RAB7B gene in keratinocytes are respectively suppressed, the amount of melanin in the keratinocytes increases. Furthermore, the increase in the amount of melanin in keratinocytes is accompanied by suppression of the expression of the expression products of the aforementioned genes. Moreover, through the suppression of the expression of these genes in keratinocytes, melanin localization in the vicinity of cell nuclei, which is usually recognized in keratinocytes, is inhibited, and thus melanin becomes scattered in the cytoplasm. Furthermore, excretion or decomposition of melanin is suppressed, and melanin is accumulated in cells. Also, as will be described in the Examples described below, it was confirmed that there is a high correlation between the amounts of expression of the genes described above and the color of skin. That is, ATG7 gene, RAB11A gene, CLIP-170 gene, Rubicon gene and RAB7B gene, and expression products thereof are involved in the localization, accumulation, excretion or decomposition of melanin in keratinocytes, and contribute to the regulation of the amount of melanin in cells or the control of the color of skin and hair.

The dynamics of melanin in keratinocytes, for example, the uptake, transport, localization, accumulation, excretion and decomposition of melanin that is transferred from melanocytes, are deeply involved in the amount and distribution of melanin in the skin epidermal layer that is mainly composed of keratinocytes, or in the hair matrix cells of hair follicles or hair cortex cells that constitute the hair shaft, and further affects the color of skin and hair.

Therefore, ATG7 gene, RAB11A gene, CLIP-170 gene, Rubicon gene and RAB7B gene are genes that control the color of skin or hair, which can regulate the accumulation, localization and/or decomposition of melanin in keratinocytes by changing the expression of the genes, can thereby regulate the amount and distribution of melanin in the skin epidermal layer, in the hair matrix cells of hair follicles, and in the hair cortex cells that constitute the hair shaft, and can consequently control the color of skin and hair.

A decrease in the expression of the genes that control color of skin or hair of the present invention causes an increase in the amount of melanin in keratinocytes, and thus darkens the color of the cells. On the contrary, an increase in the expression of these genes causes a decrease in the amount of melanin in keratinocytes, and thus brightens the color of the cells.

Furthermore, a decrease in the expression of the genes that control the color of skin or hair of the present invention inhibits localization of melanin in the vicinity of the cell nuclei in keratinocytes and thereby scatters melanin in the cells, or suppresses excretion or decomposition of melanin, and thus darkens the color of the cells. On the contrary, an increase in the expression of these genes promotes localization of melanin in the vicinity of the cell nuclei in keratinocytes or excretion or decomposition of melanin, and thus brightens the color of the cells.

Therefore, when the expression of the genes that control the color of skin or hair of the present invention, or the expression or activity of molecules encoded by these genes (expression products) is increased, the color of skin and hair is brightened. On the contrary, when the expression of the genes that control the color of skin or hair of the present invention, or the expression or activity of the molecules encoded by these genes (expression products) is decreased, the color of skin and hair is darkened.

The genes that control the color of skin or hair and the molecules encoded by the relevant genes (expression products) are collectively referred to as skin or hair color-controlling factors in the present specification. The relations between the skin or hair color-controlling factors and the color of skin or hair were found for the first time by the inventors of the present invention.

By changing the expression or activity of a skin or hair color-controlling factor of the present invention, the amount of accumulation, localization, excretion, decomposition and the like of melanin in keratinocytes can be changed to thereby regulate the amount of melanin therein, and the color of skin or hair can be controlled. In other words, a skin or hair color-controlling factor of the present invention can be used for the regulation of the amount of melanin in keratinocytes, or for the control of the color of skin or hair. Alternatively, the skin or hair color-controlling factor of the present invention can be used for the preparation of an agent for the regulation of the amount of melanin in keratinocytes or for the control of the color of skin or hair.

In regard to the regulation of the amount of melanin or the control of the color of skin or hair according to the present invention, the expression of at least one of the relevant genes, or the expression or activity of at least one of the molecules encoded by the relevant genes may be changed in the keratinocytes of a test subject by an arbitrary means that is conventionally used in the pertinent art.

There are no particular limitations on the means that changes the expression of the relevant gene, or the expression or activity of the relevant molecule. Examples of the means that changes gene expression include gene knockdown caused by an antisense oligonucleotide, siRNA or the like; transcription activation of a target gene by a specific promoter; insertion of a gene from an external source by using a vector; and addition of an arbitrary substance which has an action of changing the expression of a gene. Among these, the addition of an arbitrary substance which has an action of changing the expression of the relevant genes is more preferred.

Examples of the molecules encoded by the aforementioned genes include mRNAs and polypeptides that are encoded by the genes. Here, the "change in the expression or activity of a molecule" may include any condition by which the expression or activity of a molecule as a whole is changed, for example, a change in the amount of expression of the molecule, a change in the decomposition rate of the molecule, a change in the activation ratio of the molecule, and a change in the inactivation ratio of the molecule. However, the "change in the expression or activity of a molecule" preferably means a change in the amount of expression of the molecule.

Examples of the means that changes the expression or activity of a molecule include a means which changes gene expression as described above, a means which changes protein expression, a means which changes the enzymatic activity or the like of the molecule, a means which changes the interaction between the molecule and its target factor, and a means which changes the signal pathway that is under the action of the molecule. Among these, a means which changes gene expression, a means which changes protein expression, and the like are more preferred.

Examples of the test subject include a keratinocyte which has an ability to express at least one of the genes described above that are natural or genetically modified, and in which regulation of the amount of melanin is desired, and a culture product, a tissue, an organ and an animal, which all contain the keratinocytes.

The keratinocyte described above is preferably a keratinocyte that exists in the skin or hair follicles, and more preferably an epidermal keratinocyte, a hair matrix cell and a hair cortex cell. Regarding the culture product, tissue and organ that contain the keratinocyte, cultured keratinocytes, and the epidermal tissue, the hair follicle tissue, skin, and culture products thereof are preferred. The animal is preferably a human being or a non-human mammal.

According to an embodiment, the regulation of the amount of melanin, or the control of the color of skin or hair according to the present invention can be carried out in vitro by using the keratinocytes, or a culture product, a tissue or an organ containing the keratinocytes as a test subject. Preferably, the test subject is cultured keratinocytes, a cultured skin tissue, cultured epidermis, or cultured hair follicles.

According to another embodiment, in regard to the regulation of the amount of melanin, or the control of the color of skin or hair according to the present invention, an animal in which the regulation of the amount of accumulation, localization, excretion or decomposition of melanin, or the control of the color of skin or hair is desired, may be a test subject. Preferably, the relevant regulation or control can be carried out non-therapeutically for aesthetic purposes, for example, for the purposes of whitening or tanning of skin, coloring (brightening or darkening) or bleaching of hair, color restoration after bleaching, and dyeing of gray hair. The term "non-therapeutic" as used herein is a concept which does not include medical activities, that is, treatment activities directed to a human body involving a therapy.

An exemplary embodiment of the present invention is a method for increasing the amount of melanin in keratinocytes, the method comprising increasing the amount of melanin in keratinocytes where an increase in the amount of melanin is desired, by suppressing the expression of at least one gene selected from the group consisting of ATG7, RAB11A, CLIP-170, Rubicon and RAB7B, or the expression or activity of at least one of the molecules encoded by the genes in the keratinocytes.

Another embodiment is a method for reducing the amount of melanin in keratinocytes, the method comprising reducing the amount of melanin in the keratinocytes where a reduction of the amount of melanin is desired, by enhancing the expression of the relevant gene, or the expression or activity of the relevant molecule.

Another exemplary embodiment of the present invention is a method for browning or darkening the skin color of a test subject, the method comprising increasing the amount of melanin in skin keratinocytes of a test subject who desires browning or darkening of skin color, or scattering melanin in the relevant keratinocytes, by suppressing the expression of at least one gene selected from the group consisting of ATG7, RAB11A, CLIP-170, Rubicon and RAB7B, or the expression or activity of at least one of the molecules encoded by the relevant genes in the relevant skin keratinocytes. According to this method, for example, skin tanning is enabled.

Another embodiment is a method for brightening the skin color of a test subject, the method comprising reducing the amount of melanin in skin keratinocytes of a test subject who desires brightening of skin color, or limiting the localization of melanin in the relevant keratinocytes, by enhancing the expression of the relevant gene, or the expression or activity of the relevant molecule in the relevant keratinocytes. According to this method, for example, skin whitening is enabled.

Still another exemplary embodiment of the present invention is a method for browning or darkening the hair color of a test subject, the method comprising increasing the amount of melanin in hair follicle keratinocytes of a test subject who desires browning or darkening of hair color, or scattering melanin in the relevant keratinocytes, by suppressing the expression of at least one gene selected from the group consisting of ATG7, RAB11A, CLIP-170, Rubicon and RAB7B, or the expression or activity of at least one of the molecules encoded by the relevant genes in the relevant skin keratinocytes. According to this method, for example, color restoration of hair after bleaching or dyeing of gray hair is enabled.

Another embodiment is a method for brightening the hair color of a test subject, the method comprising reducing the amount of melanin in hair follicle keratinocytes of a test subject who desires brightening of hair color, or limiting the localization of melanin in the relevant keratinocytes, by enhancing the expression of the relevant gene, or the expression or activity of the relevant molecule in the relevant keratinocytes. According to this method, for example, brightening or bleaching of hair is enabled.

A substance that changes the expression or activity of the skin or hair color-controlling factor of the present invention, that is, ATG7 gene, RAB11A gene, CLIP-170 gene, Rubicon gene and RAB7B gene, or expression products thereof, is a substance which can control the color of skin or hair by changing the amount of accumulation, localization, excretion, decomposition or the like of melanin in keratinocytes, and thereby regulating the amount of melanin. Therefore, the present invention also provides a method for evaluating and/or selecting an agent for regulating the amount of melanin in keratinocytes, or an agent for the control of the color of skin or hair, by using the skin or hair color-controlling factor of the present invention.

The method for evaluating and/or selecting the agent for regulating the amount of melanin in keratinocytes according to the present invention includes administering a test substance into cells; measuring a change in the expression of at least one of the skin or hair color-controlling genes of the present invention, or the expression or activity of at least one of the molecules encoded by the relevant genes in the cells; evaluating the action of regulating the amount of melanin of the relevant test substance based on the results of the relevant measurement; and selecting the relevant test substance as an agent for regulating the amount of melanin in keratinocytes based on the results of the relevant evaluation.

The cell into which the test substance is administered may be a natural cell, or may be a genetically modified cell, and is not particularly limited, as long as the cell has an ability to express at least one of the skin or hair color-controlling genes of the present invention. The cell is preferably a cultured cell, or a cell derived from an animal tissue or organ culture product, and is more preferably a cultured human cell. Also, the cell is preferably a skin cell, more preferably an epidermal cell or a hair follicle cell, and even more preferably a human-derived cultured epidermal cell (for example, a normal human epidermal cell (Normal Human Epidermal Keratinocyte; NHEK), or a human tissue cultured hair follicle cell.

The type of the test substance is not particularly limited, and may be a natural product or a synthetic product. Also, the test substance may be a simple substance, or may be a composition or a mixture. The form of administration is dependent on the test substance, and may be any arbitrary form.

The expression of a skin or hair color-controlling gene, or the expression or activity of a molecule encoded by the relevant gene can be measured according to an arbitrary analysis method that is conventionally used in the pertinent art. Examples of the method for analyzing gene expression include a dot blotting method, a Northern Blotting method, an RNase protection assay method, a reporter assay utilizing luciferase or the like, an RT-PCR method, and a DNA microarray method.

Examples of the method for analyzing the expression or activity of a molecule encoded by a gene include a Western Blotting method, an immunostaining method, an ELISA method, and a binding assay.

A change in the expression of the relevant gene or the expression or activity of the relevant molecule caused by administration of a test substance can be evaluated on the basis of the expression of the relevant gene or the expression or activity of the relevant molecule thus measured. For example, the expression of the skin or hair color-controlling gene of the present invention or the expression or activity of a molecule encoded by the gene before and after the administration of a test substance is measured, the measured values are quantified as necessary, and then the results obtained before and after the administration can be compared. For example, the expression of the skin or hair color-controlling gene of the present invention, or the expression or activity of a molecule encoded by the gene is measured from a test substance-administered group and a non-administered group or a control substance-administered group, the measured values are quantified as necessary, and then a comparison of the results can be made between the administered group and the non-administered group, or between the administered group and the control substance-administered group. Also, for example, the expression of the skin or hair color-controlling gene of the present invention, or the expression or activity of a molecule encoded by the gene is measured by administering a test substance at different concentrations, and the difference in the measurement results caused by the concentrations of the test substance can be investigated.

A test substance which affects the expression of the relevant gene or the expression or activity of the relevant molecule can be evaluated as a substance having an action of regulating the amount of melanin in keratinocytes.

For example, a substance which suppresses the expression of the skin or hair color-controlling gene of the present invention, or the expression or activity of a molecule encoded by the relevant gene, is selected as an agent for increasing the amount of melanin in keratinocytes. The relevant agent can be used as an agent for browning or darkening of the color of skin or hair, which increases the amount of melanin in keratinocytes and thereby browns or darkens the color of skin or hair (for example, a skin tanning agent, a hair color darkening agent, an agent for restoring hair color after bleaching, or a gray hair dye). On the other hand, a substance which enhances the expression of the relevant gene or the expression or activity of the relevant molecule is selected as an agent for decreasing the amount of melanin in keratinocytes. The relevant agent can be used as an agent for brightening the color of skin or hair, which reduces the amount of melanin in keratinocytes and thereby brightens the color of skin or hair (for example, a skin whitening agent, or an agent for brightening or bleaching hair).

The present invention also provides a method for evaluating and/or selecting an agent for the control of the color of skin or hair. The relevant method includes administering a test substance into cells; measuring a change in the expression of at least one of the skin or hair color-controlling genes of the present invention, or the expression or activity of at least one of molecules encoded by the relevant genes in the cells; evaluating the action for the control of the color of skin or hair of the test substance, on the basis of the results of the relevant measurement; and selecting the relevant test substance as an agent for the control of the color of skin or hair, on the basis of the results of the relevant evaluation.

The cell used in the relevant method, the test substance, the method for measuring the expression or activity of a gene or a molecule, and the method for evaluating the measurement results are the same as described above.

A test substance which affects the expression of the relevant gene or the expression or activity of the relevant molecule, can be evaluated as a substance having a skin or hair color-controlling action, and is selected as an agent for the control of the color of skin or hair, which can be used for the control of the color of skin or hair.

For example, a substance which suppresses the expression of the skin or hair color-controlling gene of the present invention or the expression or activity of a molecule encoded by the relevant gene, is selected as an agent for browning or darkening the color of skin or hair, which increases the amount of melanin in keratinocytes and thereby browns or darkens the color of skin or hair (for example, a skin tanning agent, a hair darkening agent, an agent for restoring hair color after bleaching, or a gray hair dye). On the other hand, a substance which enhances the expression of the relevant gene or the expression or activity of the relevant molecule, is selected as an agent for brightening the color of skin or hair, which reduces the amount of melanin in keratinocytes and thereby brightens the color of skin or hair (for example, a skin whitening agent, or an agent for brightening or bleaching hair).

EXAMPLES

Hereinafter, the present invention will be more specifically described by way of Examples.

Example 1

Influence exerted by the expression of skin or hair color-controlling gene on the amount of melanin in keratinocytes 1. Isolation of Melanin MNT-1 cells of melanoma cell line were cultured at 37° C. under 5% $CO_2$, using 10% AIM-V medium and RPMI-1640 medium containing 10% FBS (fetal bovine serum) (all manufactured by Life Technologies Corp.). In order to isolate and prepare a melanosome fraction from MNT-1 cells, the MNT-1 cells cultured in a T-175 flask were collected with 0.05% Trypsin/EDTA and washed with PBS. Subsequently, 3 mL of a lysis buffer (0.1 M Tris-HCl (pH 7.5), 1% Igepal CA-630, and 0.01% SDS) was added to the cells, the mixture was gently mixed, and the mixture was stirred by shaking for one hour at 4° C. This cell extract was dispensed into 1.5-mL tubes, the extract was centrifuged at a rate of 1,000 g for 10 minutes (4° C.), and the supernatant was collected. This centrifuge operation was repeated two times in total, and the supernatant thus obtained was centrifuged at 20,000 g for 10 minutes (4° C.). The resulting pellet was washed with PBS, and the centrifuge operation was further repeated under the same conditions. The pellet thus obtained was designated as the melanosome fraction (melanin).

2. Introduction of siRNA

Normal human infant epidermis-derived epidermal cells (NHEK) were cultured at 37° C. under 5% $CO_2$, using a propagation medium for epidermal cells (Epilife (registered trademark) as a medium for propagation and using an additive for medium (Humedia-KG2) (all purchased from Kurabo Industries, Ltd.). Subsequently, the cells were seeded in a 12-well plate at a cell density of $0.75 \times 10^5$ cells/mL/well. To 100 μL of a test medium, Epilife (registered trademark) (0.5 μg/m hydrocortisone and 50 ng/mL amphotericin B were added as additives for medium), 4 L of a transfection reagent, HiPerFect (registered trademark) Transfection Reagent (QIAGEN), was added, and the mixture was thoroughly stirred.

siRNAs of CLIP-170 gene, RAB7B gene, Rubicon gene, and a control (a non-specific sequence which did not have a target gene) were purchased from Ambion Silencer Select siRNA (Ambion, Life Technologies), and each of the siRNA's was added to the mixture such that the final concentration of the transfection reagent would be 10 nM. The mixture was stirred and then left to stand at room temperature for 10 minutes, and thus siRNA-transfection reagent complexes were prepared. Each of the reagent complexes was added to each well, and then the plate was gently shaken to make the content of the wells uniform. On the next day, the medium was exchanged. It was confirmed that the expression of the target gene and/or the relevant molecule was specifically suppressed by introduction of siRNA (data not illustrated).

Two days after the introduction of siRNA, melanin that had been isolated from MNT-1 cells was added, and after 24 hours, the amount of melanin in the cells was observed, while at the same time, quantification of melanin and quantification of the expression of melanosome protein (Pmel17) based on a Western Blotting method were carried out.

3. Quantification of Melanin in Cells

Twenty-four hours after the addition of melanin, the cell culture plate was washed three times with PBS, and 120 μL of 2 M NaOH was added to each well. Subsequently, the cells were lysed therein at 100° C. The plate was centrifuged, the absorbance (405 nm) of the supernatant thus obtained was measured, and thus the amount of melanin was calculated. The amount of melanin was submitted to an evaluation after being compensated with respect to the amount of protein in each well determined by a standard method.

4. Analysis of Expression of Melanosome Protein

Twenty-four hours after the addition of melanin, the cell culture plate (12 wells) was washed with PBS, and then 0.1 mL of RIPA buffer (manufactured by Sigma-Aldrich Company) was added to the wells. The cells were collected, and the cells were crushed by ultrasonication.

Subsequently, the crushed cells were centrifuged at 15,000 rpm for 15 minutes, the supernatant was subjected to protein quantification, and then the supernatant was subjected to SDS-PAGE (12.5% gel) according to a standard method. A primary antibody used for the experiment was anti-Pmel17 antibody (HMG45, 1:500, manufactured by DAKO Corp.). A secondary antibody used for the experiment was anti-mouse IgG peroxidase linked F(AB')2 fragment (GE Healthcare Bioscience), which was used after diluting 5000 times. Thereafter, color development was carried out by using ECL Plus Western Blotting detection reagents (GE Healthcare Bioscience), and the protein was visualized by using LAS4000 (GE Healthcare Bioscience). Expression of β-actin as an internal standard was evaluated by using monoclonal antibody specific for β-actin manufactured by Sigma-Aldrich Company.

Figure 2:
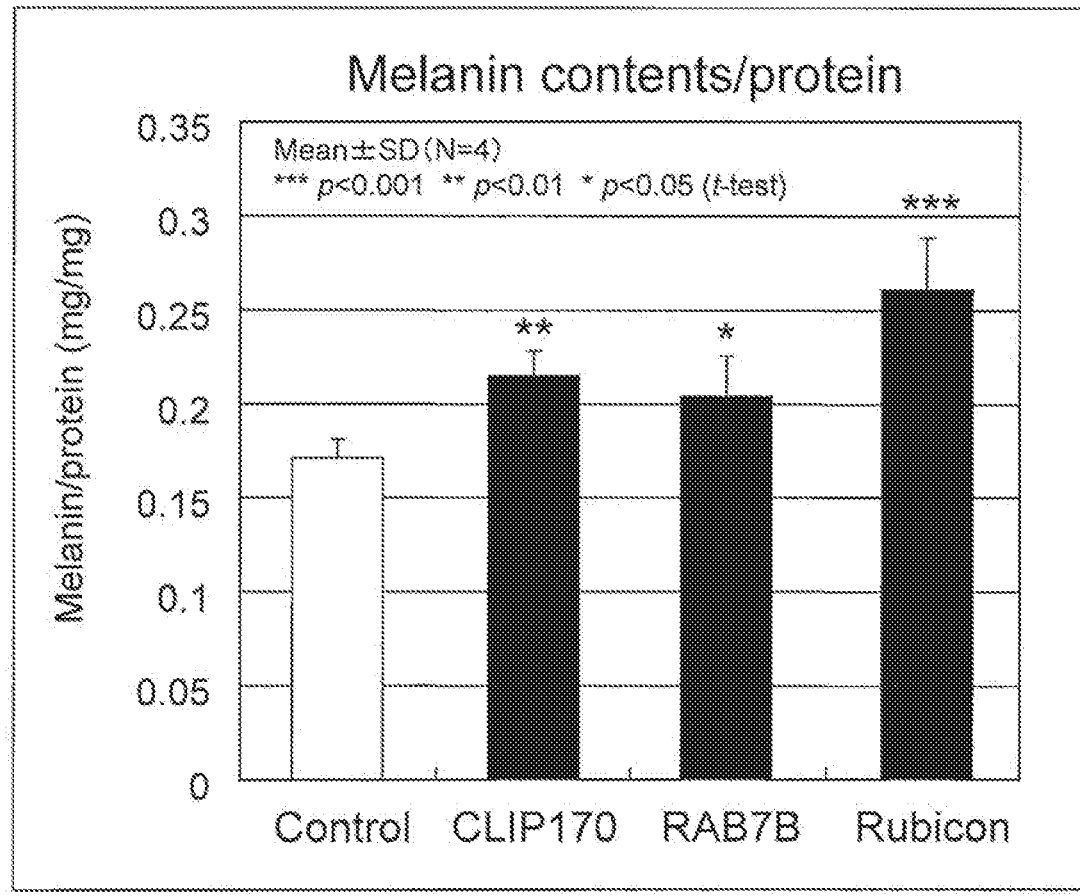
FIG. 2 is a diagram illustrating the change in the amount of melanin in keratinocytes after suppression of the expression of CLIP-170, RAB7B, or Rubicon gene.
Figure 3:
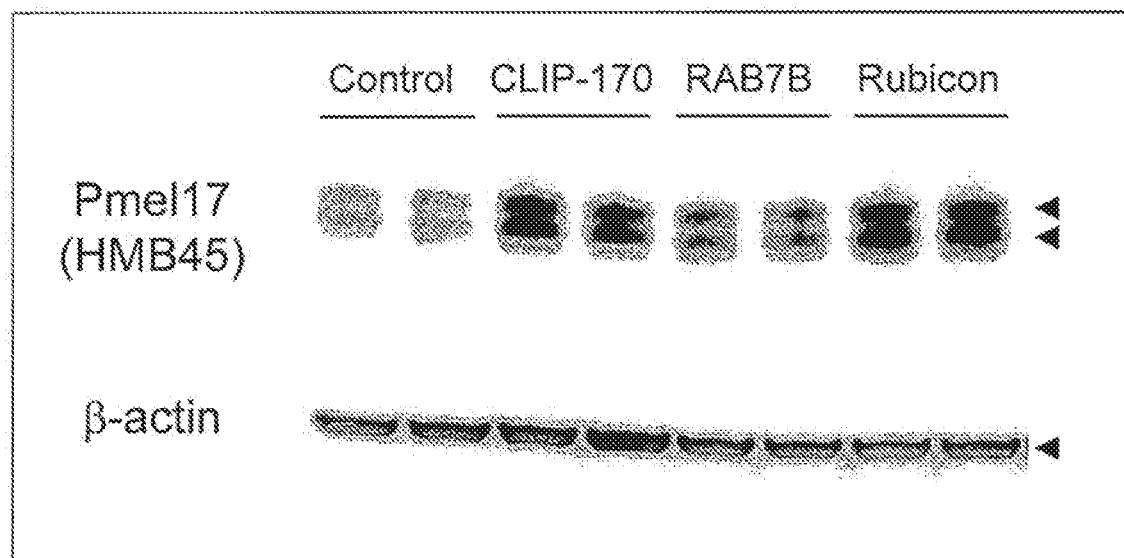
FIG. 3 is images illustrating the change in the amount of melanin (melanosome) in keratinocytes after suppression of the expression of CLIP-170, RAB7B, or Rubicon gene: Western Blotting images.

The results are presented in FIG. 1 to FIG. 3. When the expression of CLIP-170, RAB7B or Rubicon was suppressed, a change in the localization of melanin in cells was observed together with an increase in the accumulation of melanin in cells (FIG. 1). A tendency that localization of melanin in the vicinity of the nucleus, which was observed in the control, was inhibited, and melanin was scattered in the cytoplasm, was observed (FIG. 1B). Furthermore, from the results of melanin quantification (FIG. 2) and an analysis (FIG. 3) of the expression of Pmel-17 protein, which is a constituent protein of melanosome, it was found that the amount of melanin in keratinocytes was increased significantly by suppressing the expression of CLIP-170, RAB7B or Rubicon, as compared with the control.

Example 2

Change in expression of skin or hair color-controlling factor resulting from melanin addition The change in the expression of the skin color-controlling gene of the present invention caused by the melanin (melanosome) incorporated into keratinocytes was investigated. Expression of RAB7B protein and mRNA after 24 hours from the addition of melanin will be described as an example.

Protein expression was evaluated as follows. The culture plate was washed with PBS after 24 hours from the addition of melanin, and then cells were collected by using 0.1 mL of RIPA buffer (manufactured by Sigma-Aldrich Company) and were crushed by ultrasonication. Thereafter, the crushed cells were centrifuged at 15,000 rpm for 15 minutes, the supernatant was subjected to protein quantification, and then the supernatant was subjected to SDS-PAGE (12.5% gel) according to a standard method. A primary antibody used for the experiment was anti-RAB7B antibody (1:1000, manufactured by Abnova Corp.). A secondary antibody used for the experiment was anti-mouse IgG peroxidase linked F(AB')2 fragment (GE Healthcare Bioscience), which was diluted 5000 times. Thereafter, color development was carried out by using ECL Plus Western Blotting detection reagents (GE Healthcare Bioscience), and the protein was visualized by using LAS4000 (GE Healthcare Bioscience). As an internal standard, expression of β-actin was evaluated by using monoclonal antibody specific for β-actin manufactured by Sigma-Aldrich Company.

Expression of mRNA was evaluated as follows. The cultured cells were washed with PBS, and then the total RNA was extracted according to a standard method by using an RNeasy (registered trademark) Mini Kit (manufactured by Qiagen N.V.). A cDNA was synthesized by a reverse transcription reaction by using 1 μg of the total RNA thus extracted. The reverse transcription reaction was carried out according to a standard method, in a Peltier Thermal cycler manufactured by MJ Research, Inc. by using a High Capacity RNA-to-CDNA Kit (manufactured by Life Technologies, Inc.). Subsequently, an analysis of gene expression according to a Real-time PCR method was carried out by using the synthesized cDNA and a TaqMan (registered trademark) probe. The probe and primer specific to each of the genes were obtained from TaqMan Gene Expression Assays (P/N4331182) manufactured by Life Technologies, Inc. Each of the amounts of expression was evaluated after being compensated with respect to the amount of expression of an internal standard gene, RPLP0. The reaction conditions were set according to a standard method, and the reaction was carried out by using a sequence detector (ABI PRISM7500 Real Time PCR System) manufactured by Applied Biosystems, Inc.

Figure 4:
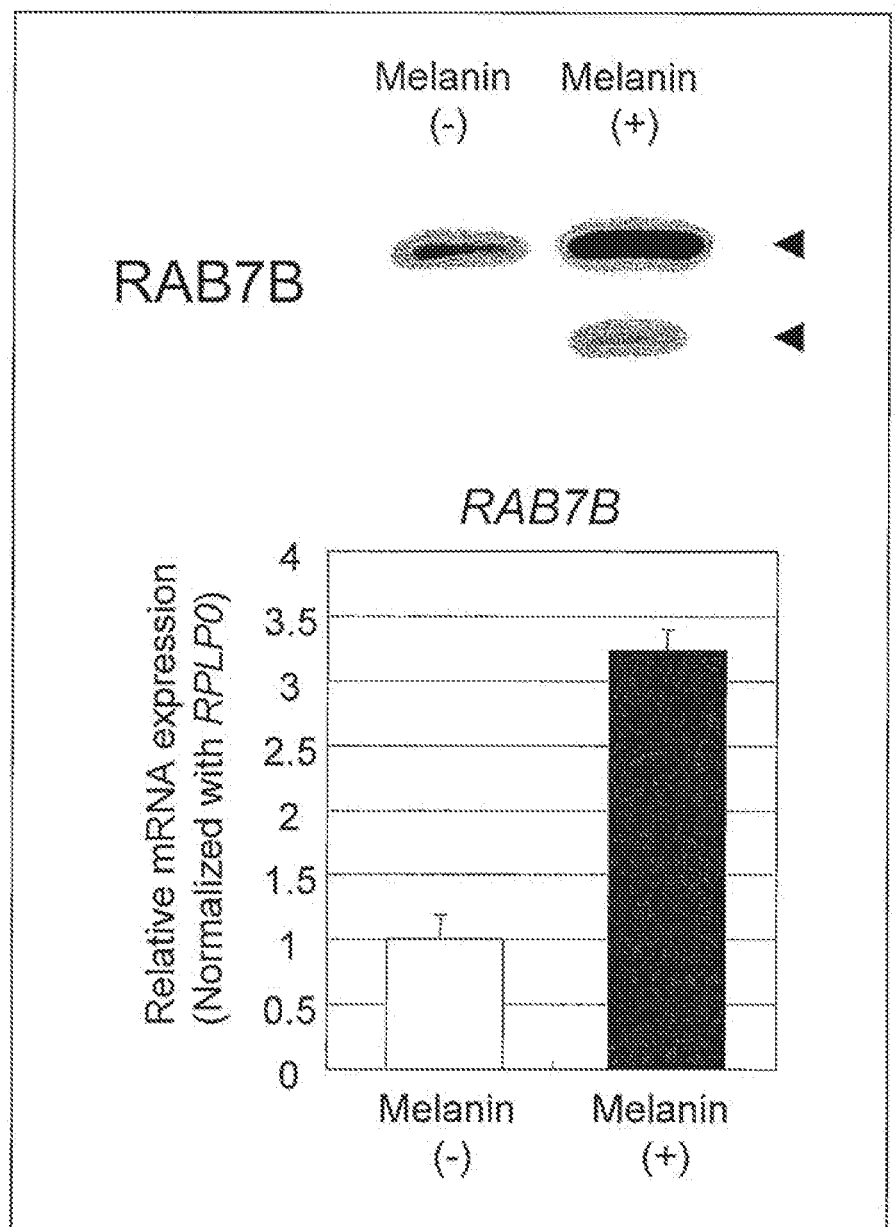
FIG. 4 is a diagram illustrating the change in the expression of RAB7B after addition of melanin.

The results are presented in FIG. 4. It was confirmed that the expression of RAB7B markedly increased at the protein and mRNA levels as a result of the addition of melanin (FIG. 4).

Example 3

Influence exerted by the expression of RAB11A or ATG7 gene on the amount of melanin in keratinocytes 1. Introduction of siRNA Normal human infant epidermis-derived epidermal cells (NHEK) were cultured at 37° C. under 5% $CO_2$, using a propagation medium for epidermal cells (Epilife (registered trademark) as a medium for propagation and using an additive for medium (Humedia-KG2) (all purchased from Kurabo Industries, Ltd.). Subsequently, the cells were seeded in a 12-well plate at a cell density of $0.75 \times 10^5$ cells/mL/well. To 100 μL of a test medium, Epilife (registered trademark) (0.5 μg/mL hydrocortisone and 50 ng/mL amphotericin B were added as additives for medium), 4 L of a transfection reagent, HiPerFect (registered trademark) Transfection Reagent (QIAGEN N.V.), was added, and the mixture was thoroughly stirred.

siRNAs of RAB11A gene, ATG7 gene, and a control (a non-specific sequence which did not have a target gene) were purchased from Ambion Silencer Select siRNA (Ambion, Life Technologies), and each of the siRNA's was added to the mixture such that the final concentration of the transfection reagent would be 10 nM. The mixture was stirred and then left to stand at room temperature for 10 minutes, and thus siRNA-transfection reagent complexes were prepared. Each of the reagent complexes was added to each well, and then the plate was gently shaken to make the content of the wells uniform. On the next day, the medium was exchanged. It was confirmed that the expression of the target gene and/or the relevant molecule was specifically suppressed by introduction of siRNA.

Two days after the introduction of siRNA, melanin that had been isolated from MNT-1 cells according to the method described in Example 1 was added, and after 24 hours, quantification of the expression of the expression products of RAB11A and ATG7 genes in the cells and the melanosome protein (Pmel17) was carried out according to a Western Blotting method. In an analysis of the expression of RAB11A and ATG7, suppression of the expression of these genes was confirmed by using anti-RAB11 antibody (1:2000, manufactured by Invitrogen, Inc.) or anti-ATG7 antibody (1:2000, manufactured by Epitomics, Inc.) as a primary antibody. The expression of β-actin as an internal standard was evaluated by using monoclonal antibody specific for β-actin manufactured by Sigma-Aldrich Company.

Figure 5:
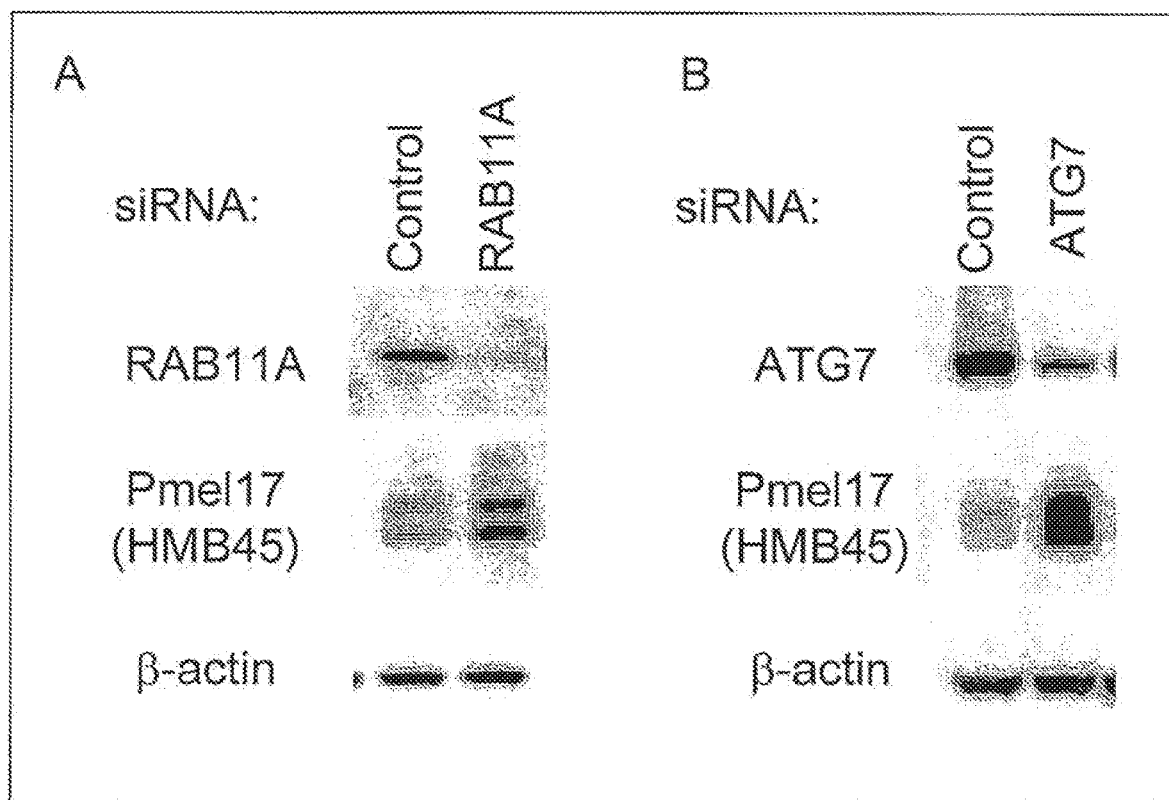
FIG. 5 is images illustrating the change in the amount of melanin (melanosome) in keratinocytes after suppression of the expression of RAB11A or ATG7 gene: Western Blotting images, in which A: Suppression of RAB11A expression, and B; Suppression of ATG7 expression.

The results are presented in FIG. 5. From the results of an analysis of the expression of Pmel-17 protein, which is a constituent protein of melanosome, it was found that the amount of melanin in keratinocytes markedly increased as compared with the control, as a result of suppressing the expression of RAB11A (FIG. 5A) or ATG7 (FIG. 5B).

Example 4

Figure 6:
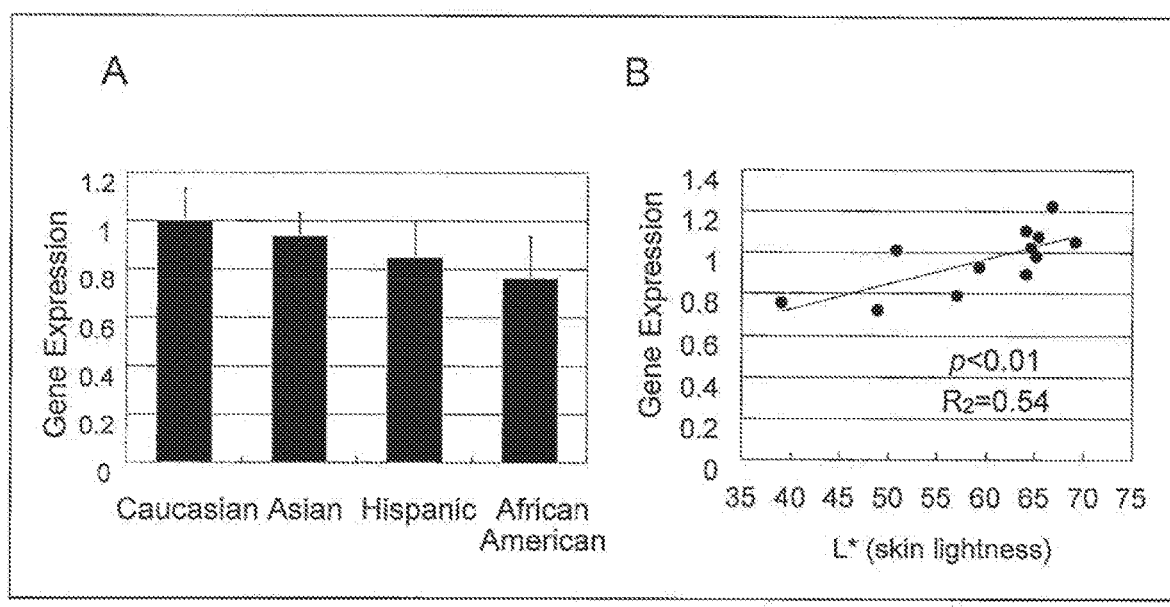
FIG. 6 is a diagram illustrating the correlation between the expression of RAB11A gene in the skin and the color of skin, in which A: Inter-racial comparison of the amount of RAB11A gene expression, and B: Correlation between the amount of RAB11A gene expression and the color of skin (L* value).

Correlation between expression of skin or hair color-controlling gene and skin color The correlation between the expression of RAB11A gene and the color of skin was investigated. The skin tissue was extracted by making a request to a contract laboratory (RCTS, Inc.) in the suburbs of Dallas, Tex., the USA, from an inner part of the upper arms of a Caucasian, an Asian, a Hispanic and an African-American (n=3 in each case) by a local dermatologist, by a punch biopsy method after the measurement of skin color. The entirety of this test was approved by IRB (IntegReview), and was carried out after providing an appropriate explanation and obtaining an agreement. After RNA was extracted from the skin tissues, the gene expression was comprehensively analyzed by a DNA microarray method using a GeneChip (Human Genome U133 plus 2.0 array) of Affymetrix, Inc., and also, the correlation between the gene expression and the intensity of skin color (lightness L* value) was investigated. The results are presented in FIG. 6.

The L* value, which is an index of the lightness of the color of skin, increased in the order of African-American, Hispanic, Asian, and Caucasian, and racial differences were confirmed (data not illustrated). Furthermore, from the results of a DNA microarray analysis, data for the expression of RAB11A gene were extracted, and it was found that RAB11A gene was expressed at an increasing level in the order of African-American, Hispanic, and Asian, as compared with Caucasian (FIG. 6A). Furthermore, a high correlation between the amount of expression of RAB11A gene and the L* value was confirmed (FIG. 6B), and it was found that as the intensity of skin color was lighter, the amount of gene expression was larger.

The invention claimed is:

1. A method for evaluating and/or selecting an agent that regulates the amount of melanin in keratinocytes, the method comprising:
   (a) administering a test substance to keratinocytes that are being cultured in medium and culturing the keratinocytes with the test substance in medium;
   (b) assaying whether, while the keratinocytes were cultured with the test substance in medium in part (a), there was a change in expression of at least one gene selected from the group consisting of ATG7, RAB11A, CLIP-170, Rubicon and RAB7B, or in the expression or activity of at least one of the molecules encoded by the gene in the keratinocytes, as compared to the expression of the gene, or as compared to the expression or activity of the molecule, in control keratinocytes that either (i) were not administered the test substance or (ii) were administered a control substance;
   (c) selecting a test substance that changes the expression of the gene or that changes the expression or activity of the molecule, in part (a) as compared to that in the control keratinocytes;
   (d) administering the test substance selected in part (c) to cells in culture to which melanosomes have been added in vitro and determining whether the amount of melanin in the cells is increased or decreased as a result of the administering and as compared to the amount of melanin in control cells that either (i) were not administered the test substance selected in part (c) or (ii) were administered a control substance; and
   (e) selecting a test substance that changes the amount of melanin in the cells of part (d) as compared to that in the control cells, as an agent that regulates the amount of melanin in keratinocytes,
   wherein a test substance that both (i) increases the amount of melanin in the cells and (ii) suppresses the expression of the gene, or the expression or activity of the molecule encoded by the gene, is an agent that regulates the amount of melanin by increasing the amount of melanin in keratinocytes; and
   wherein a test substance that both (i) decreases the amount of melanin in the cells and (ii) enhances the expression of the gene, or the expression or activity of the molecule encoded by the gene, is an agent that regulates the amount of melanin by decreasing the amount of melanin in keratinocytes.

2. A method for evaluating and/or selecting an agent that controls the color of skin or hair, the method comprising:
   (a) administering a test substance to keratinocytes that are being cultured in medium and culturing the keratinocytes with the test substance in medium;
   (b) assaying whether, while the keratinocytes were cultured with the test substance in medium in part (a), expression of at least one gene selected from the group consisting of ATG7, RAB11A, CLIP-170, Rubicon and RAB7B, or in the expression or activity of at least one of the molecules encoded by the gene in the keratinocytes, as compared to the expression of the gene, or as compared to the expression or activity of the molecule, in control keratinocytes that either (i) were not administered the test substance or (ii) were administered a control substance;
   (c) selecting a test substance that changes expression of the gene, or changes expression or activity of the molecule in part (a) as compared to that in control keratinocytes;
   (d) administering the test substance selected in part (c) to cells in culture to which melanosomes have been added in vitro and determining whether the amount of melanin in the cells is increased or decreased as a result of the administering and as compared to the amount of melanin in control cells that either (i) were not administered the test substance selected in part (c) or (ii) were administered a control substance; and
   (e) selecting a test substance that changes the amount of melanin in the cells of part (d) as compared to that in the control cells, as an agent that controls the color of skin or hair,
   wherein a test substance that both (i) increases the amount of melanin in the cells and (ii) suppresses the expression of the gene, or the expression or activity of a molecule encoded by the gene, is an agent that controls skin or hair color by darkening the color of the skin or hair; and a test substance that both (i) decreases the amount of melanin in the cells and (ii) enhances the expression of the gene, or the expression or activity of a molecule encoded by the gene, is an agent that controls skin or hair color by brightening the color of the skin or hair.

* * * * *